United States Patent [19]

Baum

[11] 4,322,535
[45] * Mar. 30, 1982

[54] PREPARATION OF ESTERS

[75] Inventor: Jonathan S. Baum, Pennington, N.J.

[73] Assignee: FMC Corporation, Philadelphia, Pa.

[*] Notice: The portion of the term of this patent subsequent to Mar. 3, 1998, has been disclaimed.

[21] Appl. No.: 233,808

[22] Filed: Feb. 12, 1981

Related U.S. Application Data

[63] Continuation-in-part of Ser. No. 159,085, Jun. 13, 1980, Pat. No. 4,254,051, which is a continuation-in-part of Ser. No. 79,635, Sep. 27, 1979, abandoned.

[51] Int. Cl.$^3$ .................. C07C 121/75; C07D 213/64
[52] U.S. Cl. ............................... 546/300; 260/465 D
[58] Field of Search .................... 260/465 D; 546/300

[56] References Cited

U.S. PATENT DOCUMENTS

| | | | |
|---|---|---|---|
| 3,835,176 | 9/1974 | Matsuo et al. | 260/465 D |
| 4,024,163 | 9/1977 | Elliott et al. | 260/465 D X |
| 4,110,361 | 8/1978 | Sheldon et al. | 260/465 D |
| 4,254,051 | 3/1981 | Baum | 260/465 D |

FOREIGN PATENT DOCUMENTS 1439615 6/1976 United Kingdom .
2000764 1/1979 United Kingdom .

OTHER PUBLICATIONS

Kirk–Othmer, "Encyclopedia of Chemical Technology", vol. 19, The Interstate Encyclopedia, Inc., New York, N.Y., 1969, pp. 564–566.

*Primary Examiner*—Dolph H. Torrence
*Attorney, Agent, or Firm*—R. L. Hansen; H. R. Ertelt

[57] ABSTRACT

Certain alpha-cyano esters are prepared by reacting an acyl halide with an aldehyde in a substantially water-immiscible aprotic solvent and an aqueous solution of water-soluble cyanide salt in the presence of an amphoteric surfactant rate-promoting agent.

10 Claims, No Drawings

PREPARATION OF ESTERS

This is a continuation-in-part of application Ser. No. 159,085, filed June 13, 1980, U.S. Pat. No. 4,254,051, which in turn is a continuation-in-part of application Ser. No. 79,635, filed Sept. 27, 1979, abandoned.

This invention relates to a process for preparing esters of carboxylic acids, more specifically, esters which contain a cyano group bonded to the alpha-carbon atom in the alcohol portion of the ester molecule.

Esters with a cyano group so situated are prepared by reacting an acid with the appropriate cyanohydrin. According to U.S. Pat. No. 3,835,176, the reaction can also be effected by treating an acyl halide with a mixture of the appropriate aldehyde and aqueous sodium or potassium cyanide, optionally in an aprotic solvent. It is disclosed, for example, that 3-phenoxy-α-cyanobenzyl chrysanthemate is prepared in 64% yield by reacting chrysanthemoyl chloride, 3-phenoxybenzaldehyde, and an aqueous solution of sodium cyanide at 0° C. for 1 hour.

U.S. Pat. No. 4,110,361 discloses a variation of this process which employs, in addition to the acyl halide, the aldehyde, and the water-soluble cyanide, a mixture of water, a water-immiscible aprotic solvent, and a surface-active agent as catalyst. Using a preferred nonionic poly(ethyleneoxy) compound as the catalyst, for example, the commercial insecticidal ester, α-cyano-3-phenoxybenzyl 3-(2,2-dichloroethenyl)-2,2-dimethylcyclopropanecarboxylate, is prepared in 80% yield at room temperature in a reaction time of 2 hours. Were it possible to shorten the reaction time and increase the yield, producing this and other alpha-cyano esters by reacting an acyl halide with an aldehyde and a cyanide would be of great commercial interest. Insecticidal alpha-cyano esters whose preparations would be facilitated include α-cyano-3-phenoxybenzyl 3-(2,2-dichloroethenyl)-2,2-dimethylcyclopropanecarboxylate and α-cyano-3-phenoxybenzyl 3-(2,2-dibromoethenyl)-2,2-dimethylcyclopropanecarboxylate, whose insecticidal activity is disclosed in U.S. Pat. No. 4,024,163, incorporated by reference herein. Other insecticidal alpha-cyano esters of particular interest are α-cyano-3-phenoxybenzyl 3-(2-chloro-3,3,3-trifluoropropenyl)-2,2-dimethylcyclopropanecarboxylate, α-cyano-3-phenoxybenzyl 2,2,3,3-tetramethylcyclopropanecarboxylate, and α-cyano-3-phenoxybenzyl 2-(4-chlorophenyl)-3-methylbutanoate, whose activity is disclosed in Great Britain Pat. No. 2,000,764, U.S. Pat. No. 3,835,176, and Great Britain Pat. No. 1,439,615, respectively, all of which are incorporated herein by reference. Still other insecticidal alpha-cyano esters of particular interest are cyano(3-phenoxyphenyl)methyl 4-difluoromethoxy-α-(1-methylethyl)-benzeneacetate, cyano(4-fluoro-3-phenoxyphenyl)methyl 3-(2,2-dichloroethenyl)-2,2-dimethylcyclopropanecarboxylate, cyano(6-phenoxypyrid-2-yl)methyl 3-(2,2-dichloroethenyl)-2,2-dimethylcyclopropanecarboxylate, and cyano(3-phenoxyphenyl)methyl 2-[(2-chloro-4-trifluoromethylphenyl)amino]-3-methylbutanoate, as well as cyano[3-(4-halophenoxy)phenyl]methyl 3-(2,2-dichloroethenyl)-2,2-dimethylcyclopropanecarboxylates, wherein halo is fluorine, chlorine, or bromine.

One advantage of this invention is that it provides a process for making alpha-cyano esters in very high yield in a short time. Another advantage of this invention is that it provides an esterification process whose product does not require lengthy and expensive purification.

Accordingly, this invention provides a method to prepare an insecticidal alpha-cyano ester by reacting an acyl halide with an aldehyde in a mixture of substantially water-immiscible aprotic solvent and an aqueous solution of water-soluble cyanide salt in the presence of a catalytic amount of amphoteric surfactant rate-promoting agent. Either the acyl halide or the aldehyde may exhibit optical or geometric isomerism, which is not affected by the reaction.

In a preferred embodiment, there is provided a process for preparing an insecticidal α-cyano-3-phenoxybenzyl ester of the formula

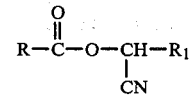

wherein R is selected from 3-(2,2-dichloroethenyl)-2,2-dimethylcyclopropyl, 3-(2,2-dibromoethenyl)-2,2-dimethylcyclopropyl, 3-(2-chloro-3,3,3-trifluoropropenyl)-2,2-dimethylcyclopropyl, 2,2,3,3-tetramethylcyclopropyl, 1-(4-chlorophenyl)-2-methylpropyl, 1-(4-difluoromethoxyphenyl)-2-methylpropyl, and 1-[(2-chloro-4-trifluoromethyl)amino]-2-methylpropyl and $R_1$ is selected from 3-phenoxyphenyl, 4-fluoro-(3-phenoxy)phenyl, 3-(4-halophenoxy)phenyl, and 6-phenoxy-2-pyridyl which comprises reacting an acyl halide of the formula

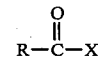

wherein X is chlorine or bromine and R is as defined above with 3-phenoxybenzaldehyde, 4-fluoro-3-phenoxybenzaldehyde, a 3-(4-halophenoxy)benzaldehyde, or 6-phenoxy-2-pyridylcarboxaldehyde in a mixture of substantially water-immiscible aprotic solvent and an aqueous solution of water-soluble cyanide salt in the presence of a catalytic amount of amphoteric surfactant rate-promoting agent selected from aminoalkylsulfonic acids.

The process of this invention is especially effective in producing a high yield of insecticidal α-cyano-3-phenoxybenzyl esters in a short time when R is 3-(2,2-dichloroethenyl)-2,2-dimethylcyclopropyl, or 1-(4-chlorophenyl)-2-methylpropyl, and outstanding results are obtained when R is 3-(2,2-dichloroethenyl)-2,2-dimethylcyclopropyl.

Although the process of this invention is especially advantageous when R is selected from the groups named above, the process is also effective in producing other alpha-cyano esters wherein R is an aliphatic or aromatic group, which may optionally contain various substituents. Although the process of this invention is preferably employed to produce α-cyano-3-phenoxybenzyl esters by using 3-phenoxybenzaldehyde as a reactant, the process is equally suited to the production of other alpha-cyano esters by varying the type of aldehyde employed in the process.

Various aprotic solvents which are substantially water-immiscible may be used in the process. Any alkyl, haloalkyl, aryl, haloaryl, aralkyl, haloaralkyl, or cyclic hydrocarbon, provided that it is a liquid at temperatures between about 0° C. and 50° C. and forms a discrete second phase when mixed with water, may be used. Such solvents include iso-hexane, 3-methylpentane, 2,3-dimethylbutane, 2,2-dimethylbutane, n-heptane, n-octane, petroleum ether, ligroin, n-propyl bromide, n-propyl iodide, n-butyl chloride, n-butyl bromide, n-pentyl chloride, n-pentyl bromide, diethyl ether, dipropyl ether, dibutyl ether, benzene, toluene, and xylene, for example. Among these solvents, n-heptane is preferred because it is readily available and inexpensive.

A number of water-soluble cyanide salts may be used; for example, the salt may be an alkali metal cyanide such as lithium, sodium, potassium, rubidium, or cesium cyanide, or mixtures thereof. Among these, sodium cyanide generally is preferred.

The cyanide salt is dissolved in water, the amount of water employed being relatively small, but preferably sufficient to keep all of the cyanide salt in solution under the reaction conditions. In the case that the salt is sodium cyanide, the preferred molar ratio of water to sodium cyanide is between about 3.5 and 6, preferably about 4.5.

The process of this invention is conducted in the pressence of a catalytic amount of rate-promoting agent selected from amphoteric surfactants, especially aminoalkylsulfonic acids. For purposes of this invention, a catalytic amount of rate-promoting agent is in the range 1–5 mole percent based on aldehyde, advantageously about 2 mole percent. Further, for purposes of this invention and wherever it appears in the specification or claims, the term "aminoalkylsulfonic acids", means compounds having the structural formula

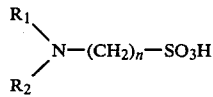

wherein n is 2 or 3, and wherein $R_1$ and $R_2$ are substituents selected collectively to render the aminoalkylsulfonic acids soluble in water-immiscible aprotic solvents. Suitable substituent groups, which collectively contain hydrocarbon units, are present in the following specific aminoalkylsulfonic acids: 1,4-piperazinebisethanesulfonic acid, 4-pyridineethanesulfonic acid, 2-[N,N-di-(2-hydroxy)ethyl]aminoethanesulfonic acid, 3-(cyclohexylamino)propanesulfonic acid, 2-[4-(2-hydroxyethyl)-piperizine-1-yl]ethanesulfonic acid, 2-(N-morpholino)ethanesulfonic acid, N-tris(hydroxymethyl)methyl-2-aminoethanesulfonic acid, 2(N-morpholino)propanesulfonic acid, and N-tris(hydroxymethyl)methyl-2-aminoethanesulfonic acid. Among these compounds, 1,4-piperizinebisethanesulfonic acid and 3-(cyclohexylamino)propanesulfonic acid are preferred, and 3-(cyclohexylamino)propanesulfonic acid is especially effective.

The process of this invention is carried out between approximately equimolar amounts of the acyl halide, preferably the acyl chloride, aldehyde and aqueous solution of cyanide salt in the water-immiscible aprotic solvent, but slight excesses of the acyl halide and cyanide salt are typically used. The acyl halide may be added last, preferably dropwise, to the stirred reaction mixture, but it is preferred to add a solution containing aldehyde and acyl halide to a stirred mixture of aqueous cyanide salt and water-immiscible aprotic solvent. Although the reaction can be carried out over a wide temperature range, the range 0° C. −50° C. is satisfactory in most cases, and it is preferred to carry out the reaction at room temperature, since neither external heating nor cooling are then required.

The process will be understood more readily by reference to the following Examples, which illustrate it. Temperatures are in degrees Celsius. The reactions exemplified were, in many cases, monitored by gas liquid partition chromatography (glpc), and the time required for disappearance of the limiting reagent after beginning addition of the acyl halide was determined, together with the amount of alpha-cyano ester produced at that time.

EXAMPLE 1

Preparation of α-cyano-3-phenoxybenzyl 3-(2,2-dichloroethenyl)-2,2-dimethylcyclopropanecarboxylate A. Using 1,4-piperazinebisethanesulfonic acid as the rate-promoting agent A flask was charged with 3-phenoxybenzaldehyde (1.98 g, 10 mmole), 10 ml n-heptane, 1,4-piperazinebisethanesulfonic acid (60 mg, 0.2 mmole), sodium cyanide (0.59 g, 12 mmole), 1 ml water, and a solution of 3-(2,2-dichloroethenyl)-2,2-dimethylcyclopropanecarbonyl chloride (2.38 g, 10.5 mmole) in 10 ml n-heptane. The reaction mixture was stirred for 4.5 hours (glpc indicated a 91% yield after 1 hr, 50 min), diluted with 30 ml diethyl ether, then washed once with 1 N aqueous sodium hydroxide solution (20 ml), once with water (20 ml), and once with a saturated aqueous sodium chloride solution (20 ml). After separation, the clear yellow ethereal solution was dried over magnesium sulfate; then the solvent was evaporated to afford the desired ester (4.05 g).

B. Using 3-(cyclohexylamino)propanesulfonic acid as the rate-promoting agent (1) In the manner of Example A above, but substituting 3-(cyclohexylamino)propanesulfonic acid (44 mg, 0.2 mmole) for the 1,4-piperazinebisethanesulfonic acid, glpc indicated a 97.2% yield of the desired ester after 95 minutes and isolation afforded the desired ester (3.49 g).

In a similar experiment, glpc indicated a 99% yield of the desired ester in two hours.

(2) A stirred mixture of sodium cyanide (18.0 g, 0.36 mole) and 3-(cyanohexylamino)propanesulfonic acid (1.34 g, 0.006 mole) in 300 ml of water was warmed to 40°. During a one hour period, maintaining a reaction temperature of about 40°, a solution of cis-3-(2,2-dichloroethenyl)-2,2-dimethylcyclopropanecarbonyl chloride (71.7 g, 0.315 mole) and 3-phenoxybenzaldehyde (61.9 g, 0.3 mole) in 262.2 g of n-heptane was added. The mixture was then stirred at 40° for one additional hour, after which it was washed with an aqueous solution containing 20% sodium carbonate and then with water. The organic phase was separated from the mixture and the solvent removed by distillation under reduced pressure to give α-cyano-3-phenoxybenzyl cis-3-(2,2-dichloroethenyl)-2,2-dimethylcyclopropanecarboxylate.

The substitution of other rate-promoting agents under otherwise similar conditions gave the following yields (glpc) after the indicated reaction times.

| Rate-Promoting Agent | Reaction Time | Yield |
| --- | --- | --- |
| 2-[4-(2-hydroxyethyl)piperazine-1-yl]ethanesulfonic acid | 55 min. | 91% |
| 4-pyridineethanesulfonic acid | 2.3 hr. | 94% |

-continued

| Rate-Promoting Agent | Reaction Time | Yield |
| --- | --- | --- |
| 2-[N,N-di-(2-hydroxy)ethyl] aminoethanesulfonic acid | 3.3 hr. | 90% |

EXAMPLE 2

Preparation of α-cyano-3-phenoxybenzyl 2-(4-chlorophenyl)-3-methyl butanoate using 3-(cyclohexylamino)propanesulfonic acid as the rate-promoting agent A flask was charged with 3-(cyclohexylamino)propanesulfonic acid (42 mg), 3-phenoxybenzaldehyde (1.90 g, 9.6 mmole), sodium cyanide (0.56 g, 12 mmole), 1 ml water, and 15 ml n-heptane. 2-(4-Chlorophenyl)-3-methylbutanoyl chloride (2.34 g, 10.1 mmole) in 5 ml n-heptane was added dropwise over a period of 24 minutes to the stirred mixture. Thirty minutes after the addition was complete, a total of 54 minutes, glpc indicated a 95.6% yield of the desired ester. After stirring overnight, the reaction mixture was filtered and extracted with ether. The ether was evaporated from the extract, affording α-cyano-3-phenoxybenzyl 2-(4-chlorophenyl)-3-methyl butanoate (3.47 g).

I claim:

1. A process for preparing an insecticidal α-cyano-3-phenoxybenzyl ester of the formula

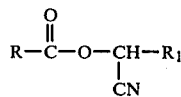

wherein R is selected from 3-(2,2-dichloroethenyl)-2,2-dimethylcyclopropyl, 3-(2,2-dibromoethenyl)-2,2-dimethylcyclopropyl, 3-(2-chloro-3,3,3-trifluoropropenyl)-2,2-dimethylcyclopropyl, 2,2,3,3-tetramethylcyclopropyl, 1-(4-chlorophenyl)-2-methylpropyl, 1-(4-difluoromethoxyphenyl)-2-methylpropyl, and 1-[(2-chloro-4-trifluoromethyl)amino]-2-methylpropyl and R₁ is selected from 3-phenoxyphenyl, 4-fluoro-(3-phenoxy)phenyl, 3-(4-halophenoxy)phenyl, and 6-phenoxy-2-pyridyl which comprises reacting an acyl halide of the formula

wherein X is chlorine or bromine and R is as defined above with 3-phenoxybenzaldehyde, 4-fluoro-3-phenoxybenzaldehyde, a 3-(4-halophenoxy)benzaldehyde, or 6-phenoxy-2-pyridylcarboxaldehyde in a mixture of substantially water-immiscible aprotic solvent and an aqueous solution of water-soluble cyanide salt in the presence of a catalytic amount of amphoteric surfactant rate-promoting agent selected from aminoalkylsulfonic acids.

2. The process of claim 1 wherein the rate-promoting agent is selected from 1,4-piperazinebisethanesulfonic acid, 4-pyridineethanesulfonic acid, 2-[N,N-di-(2-hydroxy)ethyl]-aminoethanesulfonic acid, 3-(cyclohexylamino)propanesulfonic acid, and 2-[4-(2-hydroxyethyl)piperizine-1-yl]ethanesulfonic acid.

3. The process of claim 1 wherein the rate-promoting agent is selected from 1,4-piperizinebisethanesulfonic acid and 3-(cyclohexylamino)propanesulfonic acid.

4. The process of claim 3 wherein the rate-promoting agent is 3-(cyclohexylamino)propanesulfonic acid.

5. The process of claim 1 wherein R is selected from 1-(4-difluoromethoxyphenyl)-2-methylpropyl and 1-[(2-chloro-4-trifluoromethyl)amino]-2-methylpropyl.

6. The process of claim 1 wherein the acyl halide is reacted with 4-fluoro-3-phenoxybenzaldehyde, a 3-(4-halophenoxy)benzaldehyde, or 6-phenoxy-2-pyridylcarboxaldehyde.

7. A process according to any one of claims 1, 2, 3, 4, or 6 wherein R is 3-(2,2-dichloroethenyl)-2,2-dimethylcyclopropyl or 1-(4-chlorophenyl)-2-methylpropyl.

8. A process according to any one of claims 1, 2, 3, 4, or 6 wherein R is 3-(2,2-dichloroethenyl)-2,2-dimethylcyclopropyl.

9. A process according to any one of claims 1, 2, 3, 4, 5, or 6 wherein the water-immiscible aprotic solvent is n-heptane.

10. A process according to any one of claims 1, 2, 3, 4, 5, or 6 wherein the water-soluble cyanide salt is sodium cyanide.

* * * * *